(12) United States Patent
Kagan et al.

(10) Patent No.: US 6,649,779 B2
(45) Date of Patent: Nov. 18, 2003

(54) ESTRENES

(75) Inventors: Michael Z. Kagan, Plainsboro, NJ (US); Fangming Kong, Westwood, NJ (US); Leonard A. McDonald, Mountainside, NJ (US); Panolil Raveendranath, Monroe, NY (US); Syed M. Shah, East Hanover, NJ (US); Joseph Zeldis, New City, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/162,972

(22) Filed: Jun. 5, 2002

(65) Prior Publication Data

US 2002/0151532 A1 Oct. 17, 2002

Related U.S. Application Data

(63) Continuation of application No. 09/063,585, filed on Apr. 21, 1998, now abandoned.
(60) Provisional application No. 60/046,817, filed on May 2, 1997.

(51) Int. Cl.$^7$ .................................................. C07J 1/00
(52) U.S. Cl. ........................................................ 552/644
(58) Field of Search ............................ 514/178; 552/644

(56) References Cited

U.S. PATENT DOCUMENTS

| | | | |
|---|---|---|---|
| 2,834,712 A | | 5/1958 | Beall et al. |
| 3,087,943 A | * | 4/1963 | Johns ..................... 260/397.4 |
| 3,589,981 A | | 6/1971 | Berndt et al. |
| 3,608,077 A | | 9/1971 | Ginsig |
| 4,154,820 A | | 5/1979 | Simoons |

OTHER PUBLICATIONS

Johns, J. Org. Chem., vol. 29, pp. 1490–1494, 1964.*
Physicians' Desk Reference, 48th Edition, pp. 2594–2596, 1994.*
Goodman and Gilman, p. 1420, col. 1, lines 5–12, 1985.*
Tanabe K.. et al., Chem Pharm Bull, 1967, 15(1), pp. 27–37.
Garrett, W.M. et al., Endocrinology, 1991, 129(6), pp. 2941–2950.
Suginome, H. et al., J. Chem Soc Perkin Trans 1, 1990, pp. 2199–2205.
Koch, H.–J. et al., Chem Ber, 1979, 103, pp. 603–609.
Chemical Abstracts, 114(25) abstract No. 240841, p. 121, col. 1.
Townsley, J.D., et al., Biochemistry, 7(1), Jan. 1968, pp. 33–40.
Dumasia, M.C., et al., Biochem. Soc. Trans., 17(6), 1989, pp. 1019–1020.
Marshall, D.E. et al., J. Ster. Biochem. and Mol. Biol., 59(3/4), Nov. 1996, pp, 281–296.
Johns, J. Org. Chem., vol. 29, pp. 1490–1496, 1964.
Physician Desk Reference, 48$^{th}$ Edition, pp. 2594–2596, 1994.
Goodman and Gilman, Seventh Edition, pp. 1420–1429, 1985.

* cited by examiner

*Primary Examiner*—Barbara P. Badio
(74) *Attorney, Agent, or Firm*—Arnold S. Milowsky, Esq.; Cozen O'Connor

(57) ABSTRACT

This invention provides a pharmaceutically acceptable salt of 3β-hydroxy-5(10)-estrene-17-one 3-sulfate ester and a pharmaceutically acceptable salt of 3α-hydroxy-5(10)-estrene-17-one 3-sulfate ester, which are useful as an estrogens.

2 Claims, No Drawings

ESTRENES

This is a continuation of application Ser. No. 09/063,585 filed on Apr. 21, 1998, in which a CPA was filed on Oct. 4, 2000, now abandoned, which claims the benefit of Provisional Application No. 60/046,817 filed on May 2, 1997, the entire disclosure of which is hereby incorporated by reference.

BACKGROUND OF THE INVENTION

The use of naturally occurring estrogenic compositions of substantial purity and low toxicity such as PREMARIN (conjugated equine estrogens) has become a preferred medical treatment for alleviating the symptoms of menopausal syndrome, osteoporosis/osteopenia in estrogen deficient women and in other hormone related disorders. The estrogenic components of the naturally occurring estrogenic compositions have been generally identified as sulfate esters of estrone, equilin, equilenin, 17-β-estradiol, dihydroequilenin and 17-β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with tris (hydroxymethyl)aminomethane (TRIS) to prevent hydrolysis is discussed in U.S. Pat. No. 4,154,820.

One of the compounds described herein, 3β-hydroxy-5 (10)-estrene-17-one 3-sulfate ester sodium salt is a minor component of PREMARIN (conjugated equine estrogens).

DESCRIPTION OF THE INVENTION

In accordance with this invention, there is provided a pharmaceutically acceptable salt of 3β-hydroxy-5(10)-estrene-17-one 3-sulfate ester, and a pharmaceutically acceptable salt of 3α-hydroxy-5(10)-estrene-17-one 3-sulfate ester. These are collectively referred to as the compounds of this invention. The structure of 3β-hydroxy-5(10)-estrene-17-one 3-sulfate ester sodium salt is shown in Scheme I as compound (9).

Pharmaceutically acceptable salts of 3β-hydroxy-5(10)-estrene-17-one 3-sulfate ester and 3α-hydroxy-5(10)-estrene-17-one 3-sulfate ester include, but are not limited to, the alkali metal salts, alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group.

As 3β-hydroxy-5(10)-estrene-17-one 3-sulfate ester sodium salt is a minor component of PREMARIN (conjugated equine estrogens), this invention also provides 3β-hydroxy-5(10)-estrene-17-one 3-sulfate ester sodium salt in greater than one percent purity. This invention further provides a compound consisting essentially of a pharmaceutically acceptable salt of 3β-hydroxy-5(10)-estrene-17-one 3-sulfate ester, a compound consisting essentially of 3β-hydroxy-5(10)-estrene-17-one 3-sulfate ester, and a compound consisting essentially of 3β-hydroxy-5(10)-estrene-17-one 3-sulfate ester sodium salt.

As used in accordance with this invention, treating covers treatment of an existing condition, ameliorating the condition, or providing palliation of the condition and inhibiting includes inhibiting or preventing the progress or development of the condition.

The compounds of this invention can be prepared from readily available starting materials as shown in Scheme I for the sodium salts of 3β-hydroxy-5(10)-estrene-17-one 3-sulfate ester (9) and 3α-hydroxy-5(10)-estrene-17-one 3-sulfate ester (8).

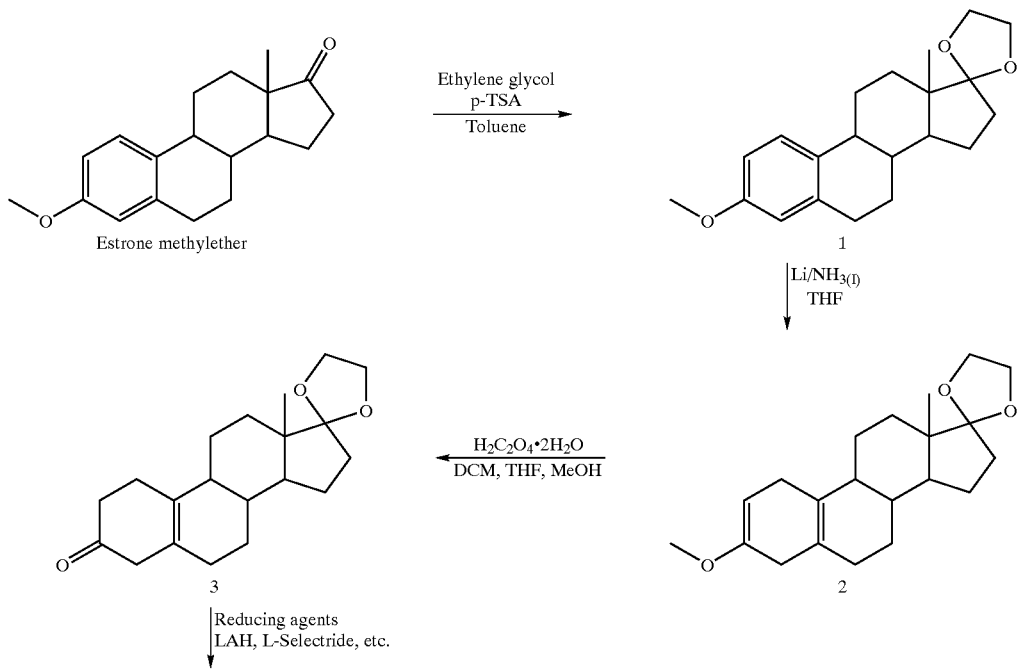

-continued

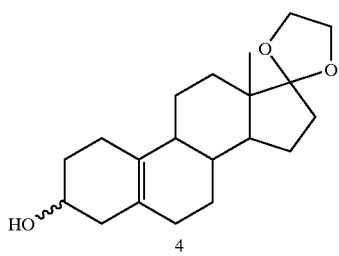
4

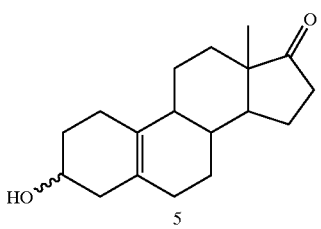
5 p-TSA
Acetone_{aq.}

SEPARATION

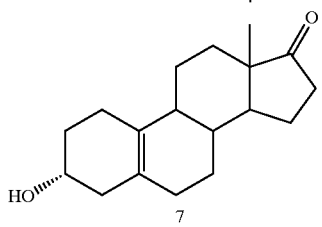
7

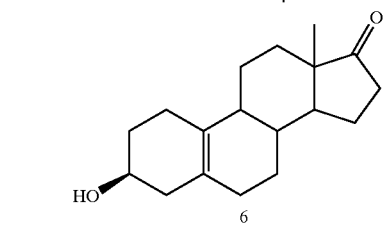
6

1. Et₃N:SO₃/THF
2. NaOH

OR

1. NaH
2. Et₃N:SO₃/THF

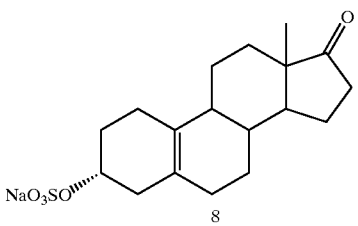
8

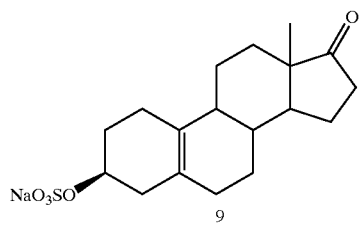
9

The compounds of this invention are estrogenic and are therefore useful in providing estrogen replacement therapy following ovariectomy or menopause, and in relieving symptoms related to estrogen deficiency, including vasomotor symptoms, such as hot flushes, and other menopausal related conditions, such as vaginal atrophy, vaginitis, and atrophic changes of the lower urinary tract which may cause increased urinary frequency, incontinence, and dysuria. The compounds of this invention are useful in preventing bone loss and in the inhibition or treatment of osteoporosis. The compounds of this invention are cardioprotective and they are useful in the treatment of atherosclerosis, ischemic disease, and hypertension. These cardiovascular protective properties are of great importance when treating postmenopausal patients with estrogens to prevent osteoporosis and in the male when estrogen therapy is indicated. The compounds of this invention are also antioxidants, and are therefore useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke. Additionally, the compounds of this invention are useful in the suppression of lactation, and in the prophylaxis and treatment of mumps orchitis.

The compounds of this invention can be used alone as a sole therapeutic agent or can be used in combination with other agents, such as other estrogens, progestins, or and androgens.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.02 $\mu$g/kg-750 $\mu$g/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A compound which is a pharmaceutically acceptable salt of 3$\beta$-hydroxy-5(10)-estrene-17-one 3-sulfate ester wherein the pharmaceutically acceptable salt of the 3-sulfate ester is an alkali metal salt, alkaline earth metal salt, ammonium salt, alkylammonium salt containing 1–6 carbon atoms, or dialkylammonium salt containing 1–6 carbon atoms in each alkyl group, or trialkylammonium salt containing 1–6 carbon atoms in each alkyl group.

2. A compound which is a pharmaceutically acceptable salt of 3$\alpha$-hydroxy-5(10)-estrene-17-one 3-sulfate ester wherein the pharmaceutically acceptable salt of the 3-sulfate ester is an alkali metal salt, alkaline earth metal salt, ammonium salt, alkylammonium salt containing 1–6 carbon atoms, or dialkylammonium salt containing 1–6 carbon atoms in each alkyl group, or trialkylammonium salt containing 1–6 carbon atoms in each alkyl group.

* * * * *

UNITED STATES PATENT AND TRADEMARK OFFICE
Certificate

Patent No. 6,649,779 B2

Patented: November 18, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Z. Kagan, Plainsboro, NJ (US); Fangming Kong, Westwood, NJ (US); Leonard A. McDonald, Mountainside, NJ (US); Panolil Raveendranath, Monroe, NY (US); Syed M. Shah, East Hanover, NJ (US); Joseph Zeldis, New City, NY (US); and Arkadiy Z. Rubezhov, West Nyack, NY (US).

Signed and Sealed this Sixteenth Day of May 2006.

SREENIVASAN PADMANABHAN
*Supervisory Patent Examiner*
Art Unit 1617